United States Patent [19]
Kick

[11] Patent Number: 5,993,374
[45] Date of Patent: Nov. 30, 1999

[54] MICROCAPSULES FOR SITE-SPECIFIC DELIVERY

[75] Inventor: George F. Kick, Laguna Hills, Calif.

[73] Assignee: Radiance Medical Systems, Inc., Irvine, Calif.

[21] Appl. No.: 08/877,593

[22] Filed: Jun. 17, 1997

[51] Int. Cl.[6] .................................................. A61M 36/00
[52] U.S. Cl. .................................................................. 600/8
[58] Field of Search .................. 600/1–8; 424/1.21–1.77

[56] References Cited

U.S. PATENT DOCUMENTS

| | | | |
|---|---|---|---|
| 2,911,338 | 11/1959 | Tabern et al. ........................... | 424/1.33 |
| 3,159,545 | 12/1964 | Kidwell et al. ........................ | 424/1.33 |
| 3,663,685 | 5/1972 | Evans et al. ............................ | 424/1.21 |
| 3,758,678 | 9/1973 | Lindsay et al. ........................ | 424/1.21 |
| 4,115,536 | 9/1978 | Rothman et al. . | |
| 4,124,705 | 11/1978 | Rothman et al. . | |
| 4,126,669 | 11/1978 | Rothman et al. . | |
| 4,225,790 | 9/1980 | Parsons, Jr. et al. . | |
| 4,247,406 | 1/1981 | Widder et al. . | |
| 4,349,529 | 9/1982 | Morcos et al. ......................... | 424/1.21 |
| 4,409,966 | 10/1983 | Lambrecht et al. . | |
| 4,674,480 | 6/1987 | Lemelson . | |
| 4,706,652 | 11/1987 | Horowitz . | |
| 4,745,907 | 5/1988 | Russel, Jr. et al. . | |
| 4,819,618 | 4/1989 | Liprie . | |
| 5,011,677 | 4/1991 | Day et al. . | |
| 5,019,369 | 5/1991 | Presant et al. . | |
| 5,081,110 | 1/1992 | Kim et al. . | |
| 5,213,561 | 5/1993 | Weinstein et al. . | |
| 5,295,962 | 3/1994 | Crocker et al. . | |
| 5,302,168 | 4/1994 | Hess . | |
| 5,302,369 | 4/1994 | Day et al. . | |
| 5,342,283 | 8/1994 | Good ......................................... | 600/8 |
| 5,411,466 | 5/1995 | Hess . | |
| 5,421,826 | 6/1995 | Crocker et al. . | |
| 5,424,288 | 6/1995 | Order ................................ | 424/1.29 X |
| 5,498,227 | 3/1996 | Mawad . | |
| 5,503,613 | 4/1996 | Weinberger . | |
| 5,609,886 | 3/1998 | Wantier et al. ..................... | 424/1.25 X |

FOREIGN PATENT DOCUMENTS

| | | |
|---|---|---|
| 1133219 | 11/1968 | United Kingdom . |
| WO 93/04735 | 3/1993 | WIPO . |

OTHER PUBLICATIONS

*Microencapsulation and Related Drug Processes*, "Solvent Evaporation Process", Patrick B. Deasey, Marcel Dekker, Inc., 1984.

(List continued on next page.)

*Primary Examiner*—Samuel Gilbert
*Attorney, Agent, or Firm*—Knobbe, Martens, Olson & Bear, LLP

[57] ABSTRACT

Disclosed is a site specific microcapsule delivery system and microcapsules for delivering one or more active agents to a preselected site. The system includes a catheter and microcapsules. A preferred embodiment of the catheter includes an inner inflatable balloon having an outer perforated delivery balloon concentrically disposed thereon. The microcapsule preferably comprises a water dissolvable core, and at least one outer protective shell. In a preferred embodiment, the core comprises phosphorous 31 and the outer shell comprises PGLA or other water soluble material. Neutron beam activation of the core produces phosphorous 32, for emitting therapeutic radiation to the treatment site. The outer protective shell dissipates over time, and, following a predetermined delivery period, the outer shell is removed and the central core dissipates to leave only biologically compatible break down products.

18 Claims, 7 Drawing Sheets

OTHER PUBLICATIONS

*Journal of the American College of Cardiology*, "Abstracts of Original Contributions", JACC, vol. 21, No. 2, Feb. 1993.

Local Drug Delivery Catheters: Functional Comparison of Porous and Microporous Designs, Charles R. Lambert, MD, PhD, James E. Leone, AB, BS, and Stephen M. Rowland, PhD, Coronary Artery Disease May 1993, vol. 4 No. 5.

*Centrifugal Extrusion Encapsulation*, "Encapsulation and Controlled Release of Food Ingredients", Chapter 9, American Chemical Society, Washington, DC 1995.

Local Intramural Drug Delivery Using an Infusion Balloon Following Angioplasty in Normal and Atherosclerotic Vessels, "Catheterization and Cardiovascular Diagnosis", vol. 31, No. 3, Mar. 1994.

A New Approach for Local Intravascular Drug Delivery (Iontophoretic Balloon). Antonio Fernandez–Ortiz, MD, PhD; Beat J. Meyer, MD; Alessandra Mailhac, MD, PhD; Erling Falk, MD; Lina Badimon, PhD; John T. Fallon, MD, PhD; Valentin Fuster, MD, PhD; James H. Chesebro, MD; Juan J. Badimon, PhD, American Heart Association, Circulation vol. 89, No. 4, Apr. 1994.

Low–Dose, β–Particle Emission From 'Stent' Wire Results in Complete, Localized Inhibition of Smooth Muscle Cell Proliferation, Tim A. Fischell, MD, Bassam K. Kharma, MD; David R. Fischell, PhD; Peter G. Loges, BS; Circulation, vol. 90, No. 6, Dec. 1994.

Endovascular Low–Dose Irradiation Inhibits Neointima Formation After Coronary Artery Balloon Injury in Swine (A Possible Role for Radiation Therapy in Restenosis Prevention), Ron Waksman, MD; Keith A. Robinson, PhD; Iam R. Crocker, MD; Michael B. Gravanis, MD; Gustavo D. Cipolla, DVM; Spencer B. King III, MD; "American Heart Association", Circulation, vol. 91, No. 5, Mar. 1, 1995.

Regional and Arterial Localization of Radioactive Microparticles After Local Delivery by Unsupported or Supported Porous Balloon Catheters, Robert L. Wilensky, MD, Keith L. March, MD, PhD, Irmina Gradus–Pizlo, MD, Donald Schauwecker, MD, PhD, MaryBeth Michaels, MS, Janine Robinson, MS, Kathy Carlson, and David R. Hathaway, MD, "American Heart Journal" (1995) vol. 129, No. 5, pp. 852–859.

Local Delivery, of Biodegradable Microparticles Containing Colchicine or a Colchicine Analogue: Effects on Restenosis and Implications for Catheter–Based Drug Delivery, Irmina Gradus–Pizlo, MD, Robert L. Wilensky, MD FACC, Keith L. March, MD, PhD, FACC, Naomi Fineberg, PhD, Marybeth Michaels, MS, George E. Sandusky, DVM, PhD David R. Hathaway, MD, FACC, "American College of Cardiology" Nov. 15, 1995, vol. 26, No. 6.

A Survey of Microencapsulation Processes, "Microencapsulation: Methods and Industrial Applications", 1996 by Marcel Dekker, Inc.

*Microspheres*, Robert L. Wilensky & Keith L. March, Semin Intervent Cardio, 1996; 1: 48–50.

Direct Intraarterial Wall Injection of Microparticles via a Catheter: A Potential Drug Delivery Strategy Following Angioplasty; Robert L. Wilensky, MD, Keith L. March, MD, PhD, and David R. Hathaway, MD, "Progress in Cardiology" American Heart Association, vol. 122, No. 4, Part 1.

Microencapsulation of Multiple Drugs, "Life Sciences" Lyndon B. Johnson Space Center, Houston Texas, NASA Tech Briefs, Nov. 1996.

The Art and Science of Microencapsulation, Southwest Research Institute, San Antonio, Texas, Reprinted from the Jun. 1995 issue of "Technology Today", Brochure.

The Making of Microcapsules, Southwest Research Institute, San Antonio, Texas, Reprint from Sep. 1989 Edition of "Technology Today", Brochure.

Abstracts from the 66th Scientific Sessions, Georgia World Congress Center, Atlanta, Georgia, Nov. 8–11, 1993, American Heart Association, Supplement to Circulation, vol. 88, No. 4, Part 2, Oct. 1993.

The Dose Distribution Produced by a $^{32}$P–coated stent, W.V. Prestwich and T.J. Kennett, F.W. Kus, Medical Physics, vol. 22, No. 3, Mar. 1995.

Abstracts From the 67th Scientific Sessions, Dallas Convention Center, Dallas, TX, Nov. 14–17, 1994, American Heart Association, Circulation, vol. 90, No. 4, Part 2, Oct. 1994.

Pure β–Particle–Emitting Stents Inhibit Neointima Formation in Rabbits, Brief Rapid Communications, Circulation, vol. 93, No. 4, Feb. 15, 1996.

Prophylactic Endovascular Radiotherapy to Prevent Intimal Hyperplasia after Stent Implantation in Femoropopliteal Arteries, Dieter Liermann, Heinz D. Bottcher, Jurgen Kollath, Bernd Schopohl, Gerd Strassmann Ernst–P. Strecker, Karl H. Breddin, CardioVascular and Interventional Radiology, (1994) 17:12–16.

Intracoronary Irradiation Markedly Reduces Restenosis After Balloon Angioplasty in a Porcine Model, Joseph G. Wiedermann, MD, Charles Marboe, MD, Howard Amols, PhD, Allan Schwartz, MD, FACC, Judah Weinberger, MD, PhD, FACC, American College of Cardiology, JACC, vol. 23, No. 6, May 1994: 1491–8.

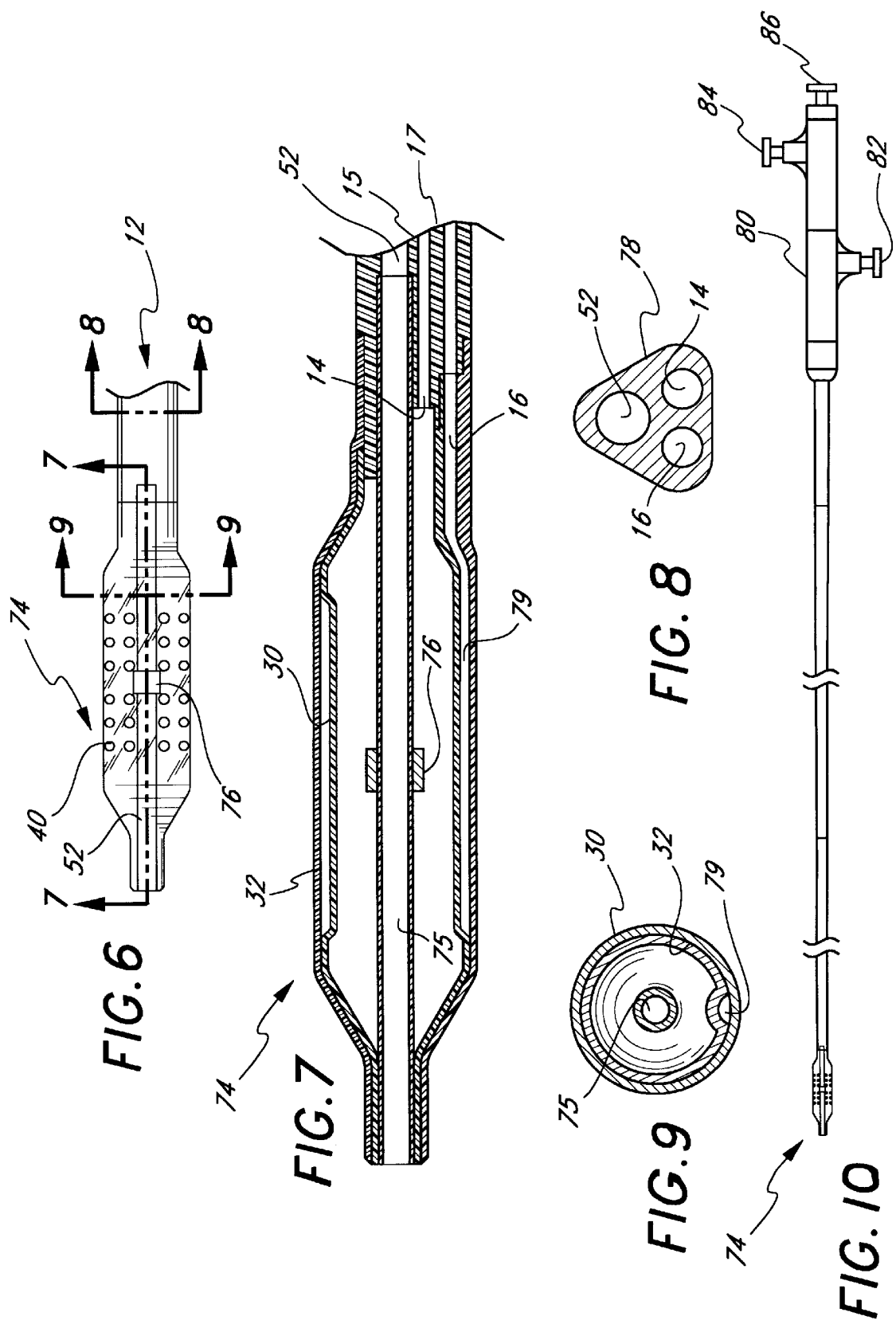

MICROCAPSULES FOR SITE-SPECIFIC DELIVERY

BACKGROUND OF THE INVENTION

The present invention relates to the treatment or prevention of vascular proliferative disorders, such as restenosis following angioplasty or other vascular trauma. The invention also relates to treatment or prevention of other disorders, such as benign or malignant cancers. Microcapsules containing an active inner core and a protective outer shell capable of delivering a therapeutic dosage of radiation or other active agent are delivered directly to a treatment site.

Vascular proliferative disorders are conditions within the walls of blood vessels, including arteries and veins, which result in occlusion or blockage of blood flow. These conditions may result from injuries or wall alterations incurred during surgical intervention, for example during angioplasty, atherectomy, graft or shunt implantation, or coronary by-pass surgery.

One common vascular proliferative disorder is stenosis of coronary arteries due to the build-up of atherosclerotic plaque on the arterial wall. Several minimally invasive procedures such as balloon angioplasty have been developed to allow the lumen of the vessel to be reopened or enlarged. One of the chief problems with treatment by mechanical dilatation is that restenosis of the vessel generally occurs due to smooth muscle cell proliferation or the occurrence of intimal hyperplasia.

Treatment of such sites with radiation is believed to be effective in decreasing restenosis. One such method of radiotherapy is implantation of a stent containing a radioisotope source at the site of the stenosis. For example, U.S. Pat. No. 5,059,166 to Fischell et al. discloses a stent where the radioisotope source is contained either in the surface coating of the stent or in the metal alloy that forms the stent. Two primary limitations on the use of such stents are that the dosage of the stent cannot be increased or decreased once it has been implanted, and that current stents are as a practical matter permanent implants that remain in place for the lifetime of the patient.

Another method of radiotherapy is the use of a radioactive catheter or wire. For example, U.S. Pat. No. 5,199,929 to Dake et al. discloses a catheter with a radioisotope source permanently attached to the distal end. The primary limitations on the use of such devices are that the source of radiation is not in uniform radiation delivery contact with all of the surfaces that require treatment and that treatment continues only as long as the catheter remains in the patient's body.

Thus, a need remains for an improved method and devices to effect a site-specific treatment for vascular proliferative disorders. There also remains a need for methods and devices to treat other conditions, such as cancer and cellular disorders, which are believed to benefit from localized radiation exposure.

SUMMARY OF THE INVENTION

There is provided in accordance with one aspect of the present invention a method of delaying restenosis of the type caused by smooth muscle cell proliferation through an injury in a vessel wall. The method comprises the steps of identifying an injury in a vessel wall, of the type associated with restenosis of the vessel due to smooth muscle cell proliferation. A delivery catheter is provided, having an elongate flexible tubular body, an inner inflatable balloon mounted on the distal end of the tubular body and an outer delivery balloon disposed coaxially about the inflatable balloon.

The catheter is positioned in the vessel so that the delivery balloon is adjacent the injury, and the inner inflatable balloon is inflated to bring the delivery balloon into contact with the injury. Radioactive microcapsules are infused through the delivery balloon and into the injury, the microcapsules having an inner core of a first material and an outer protective shell of a second material. The catheter is thereafter removed from the vessel.

In accordance with a further aspect of the present invention, there is provided a method of treating a site within a vessel. The method comprises the steps of locating a stenosis in the vessel, and positioning a delivery and dilatation balloon catheter within the stenosis. The balloon catheter comprises an expandable inner balloon and a porous outer balloon with a plurality of delivery ports about the surface of the outer balloon. The stenosis is dilated by inflating the expandable inner balloon, and infusate is delivered through the delivery ports on the porous outer balloon. The infusate comprises radioactive microcapsules suspended in a physiologically acceptable media. The expandable inner balloon is thereafter deflated, and the double balloon catheter is removed from the vessel.

In accordance with another aspect of the present invention, there is provided a microcapsule for therapeutic and/or diagnostic use. The microcapsule comprises a transient radioactive central core, and a transient outer shell surrounding the central core. The central core and the outer shell break down in an aqueous environment into biologically compatible break down products. In one embodiment, the central core comprises a phosphorous isotope, and the outer shell comprises PGLA. Additional coatings on the outer shell may also be provided, such as heparin to inhibit clot formation or coatings which improve adhesion of the microcapsules to the vessel wall.

In accordance with another aspect of the present invention, there is provided a method of providing sustained release of an active agent at a preselected, target site. The method comprises the steps of providing a core capable of delivering the active agent over time, and coating the core with a water soluble protective shell to produce a microcapsule. The microcapsule is administered to the preselected site and the protective shell is permitted to dissipate thereby exposing the core. The core is thereafter permitted to dissipate, and active agent is delivered from the core to the preselected site through at least part of the step of permitting the core to dissipate.

In accordance with a further aspect of the present invention, there is provided a method of delivering radiation to a treatment site in an aqueous environment using a carrier which dissipates following delivery of the radiation. The method comprises the steps of providing a core comprising a material which dissipates in blood and preferably comprise a radioactive material or a material capable of activation to yield a radioactive substance. The core is treated to increase the longevity of the core in a blood environment. The treated core is thereafter exposed to an activation source to activate the core material so that it emits ionizing radiation. The radioactive core is introduced to the treatment site, and radiation is expressed from the core. The core is permitted to dissipate following delivery of radiation.

Preferably, the providing of a core step comprises providing phosphorous 31. The treating the core step preferably comprises surrounding the core with a protective shell. In one embodiment, the protective shell comprises PGLA. The exposing the treated core step in one embodiment comprises exposing the core to a neutron beam.

Further features and advantages of the present invention will become apparent to those of skill in the art in view of the detailed description of preferred embodiments which follows, when considered with the attached drawings and claims.

BRIEF DESCRIPTION OF THE DRAWINGS

FIG. 6 is a partial sectional side elevational view of a non-stent embodiment of the present invention.

FIG. 7 is a cross-sectional view taken along the lines 7—7 in FIG. 6.

FIG. 8 is a cross-sectional view taken along the lines 8—8 in FIG. 6.

FIG. 9 is a cross-sectional view taken along the lines 9—9 in FIG. 6.

FIG. 10 is a side elevational view of a non-stent embodiment of the present invention in communication with a fluid delivery and guide-wire entry apparatus.

DETAILED DESCRIPTION OF THE PREFERRED EMBODIMENT

Figure 1:
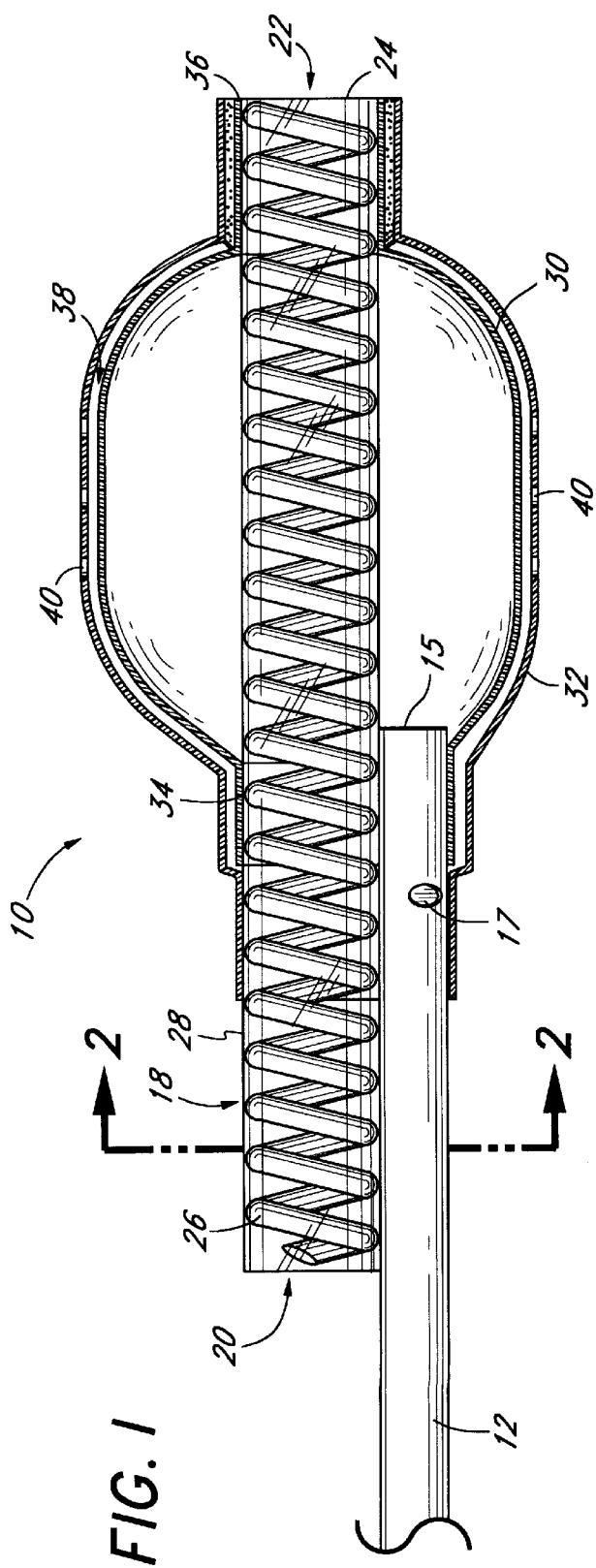
FIG. 1 is a partial sectional side elevational view of an infusate delivery and temporary stent catheter in accordance with one aspect of the present invention.

Referring to FIG. 1, there is disclosed a combination delivery and temporary stent catheter in accordance with one aspect of the present invention. The delivery capacity of such catheter and all catheters disclosed herein is to be used to effect a site-specific release of an infusate. Although one embodiment of the present invention incorporates both the delivery and temporary stent features, catheters incorporating only a single of these features can also be readily produced in accordance with the disclosure herein, as will be appreciated by one of skill in the art. In addition, the catheter of the present invention can readily be used for angioplasty dilatation as well.

The preferred infusate for the purpose of the present invention includes microcapsules having an inner core encased within an outer shell. The outer shell may comprise one or multiple layers as will be discussed. The inner core preferably comprises an active agent. The outer shell comprises a transient material and may also comprise the same or a different active agent. The microcapsules are preferably suspended in a physiologically acceptable delivery media.

The term active agent is intended to be used in a broad sense to include any of a wide variety of radioactive species, drugs, medications, or other therapeutic or diagnostic agents which are an operative part of the infusate. The term transient material is used herein to mean a material or composition which is dissolvable, biodegradable, bioabsorbable, or in some other way retains its structural integrity only temporarily in the body in its original solid or gel form before it breaks down and dissipates.

The catheter 10 generally comprises an elongate tubular body 12 for extending between a proximal control end (not illustrated) and a distal functional end. Tubular body 12 may be produced in accordance with any of a variety of known techniques for manufacturing balloon tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall as is well understood in the catheter and guidewire arts.

In general, tubular body 12, in accordance with the present invention, has a generally circular cross-sectional configuration having an external diameter within the range of from about 0.030 inches to about 0.065 inches. Alternatively, a generally triangular cross sectional configuration can also be used, with the maximum base to apex distance also within the range of from about 0.030 inches to about 0.065 inches. Other non circular configurations such as rectangular or oval may also be used. In peripheral vascular applications, the body 12 will typically have an outside diameter within the range of from about 0.039 inches to about 0.065 inches. In coronary vascular applications, the body 12 will typically have an outside diameter within the range of from about 0.030 inches to about 0.045 inches.

Diameters outside of the preferred ranges may also be used, provided that the functional consequences of the diameter are acceptable for a specified intended purpose of the catheter. For example, the lower limit of the diameter for tubular body 12 in a given application will be a function of the number of fluid or other functional lumen contained in the catheter, together with the acceptable flow rate of dilatation fluid or infusate to be delivered through the catheter.

In addition, tubular body 12 must have sufficient structural integrity (e.g., "pushability") to permit the catheter to be advanced to distal vascular locations without buckling or undesirable bending of the tubular body 12. The ability of the body 12 to transmit torque may also be desirable, such as in embodiments having an infusate delivery capability on less than the entire circumference of the delivery balloon. Larger diameters generally have sufficient internal flow properties and structural integrity, but reduce perfusion in the artery in which the catheter is placed. In addition, increased diameter catheter bodies tend to exhibit reduced flexibility, which can be disadvantageous in applications requiring placement of the distal end of the catheter in a remote vascular location.

Figure 2:
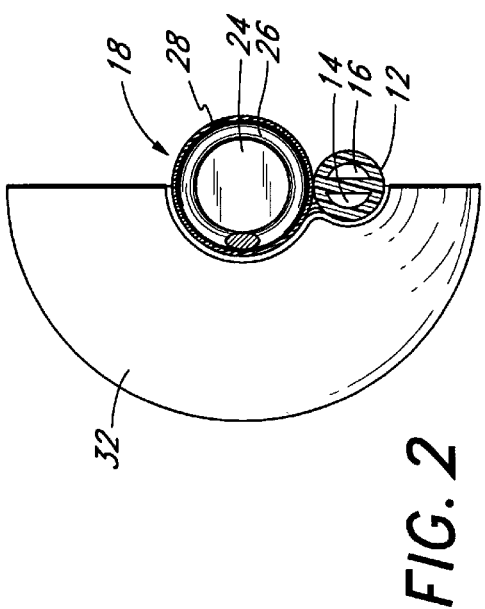
FIG. 2 is a cross sectional view taken along the lines 2—2 of FIG. 1.

As can best be seen by reference to FIG. 2, the tubular body 12, in accordance with the illustrated embodiment of the present invention, preferably comprises at least a first lumen 14 and a second lumen 16 extending axially therethrough. Inflation lumen 14 is in fluid communication with the interior of inflation balloon 30 by way of port 15. Infusate delivery lumen 16 is in fluid communication with a delivery balloon 32 by way of port 17. In this manner, inflation fluid or fluid infusate can be selectively introduced into the inflation balloon 30 and delivery balloon 32, as will be described in greater detail infra.

Additional lumen can readily be formed in tubular body 12 by techniques known in the art. In one embodiment of the present invention (not illustrated), a third lumen is provided having an opening at its proximal end and a closed distal end. This third lumen receives a wire to improve pushability of the catheter. A further embodiment, illustrated in FIG. 5 and discussed infra, is provided with a guidewire lumen for over-the-wire manipulation.

In an alternate embodiment of the catheter body, two or more lumens are disposed in a concentric arrangement. See FIGS. 3 and 4. Tubular body 12 comprises an outer tubular wall 42 defining a first lumen 44 for communicating a fluid to the distal end of the catheter. An inner tubular wall 46 defines a second lumen 48. In the illustrated embodiment, inner lumen 48 is in fluid communication with the inflation balloon 30, and outer lumen 44 is in fluid communication with the delivery balloon 32. Concentric lumen catheter bodies can be manufactured in accordance with techniques known in the art.

In the illustrated embodiment, a temporary stent 18 is secured to the distal end of tubular body 12. However, other perfusion designs may be used with the infusate delivery catheter of the present invention, such as those disclosed in U.S. Pat. No. 5,344,402 issued Sep. 6, 1994 to Crocker, the disclosure of which is hereby incorporated by reference.

As illustrated in FIG. 1, the longitudinal axis of temporary stent 18 is laterally displaced from the longitudinal axis of tubular body 12. Stent 18 generally comprises a first end 20, a second end 22 and a lumen 24 extending therebetween (See FIG. 2). Blood flow through lumen 24 can occur in either direction, depending upon the location of percutaneous insertion and the direction of transluminal travel of the catheter.

In general, it is desired that the ratio of the interior cross-sectional area of lumen 24 to the maximum exterior cross-sectional area of the deflated balloon be maximized in order to optimize perfusion across the inflation balloon 30 while inflation balloon 30 is inflated. Catheters embodying the present invention having a perfusion deflated profile of 0.055 inches or greater can be produced having an interior lumen 24 with an interior diameter of at least about 0.030 inches, and preferably about 0.039 inches or greater. This fits readily within the lumen of a guide catheter, which may have an internal diameter of about 0.072 inches. Alternatively, the diameter of lumen 24 can be reduced to as low as about 0.012 inches and still function as a guidewire conduit.

In one embodiment of the present invention, the interior diameter of lumen 24 is about 0.039 inches (1 mm). This lumen will typically provide a flow at 80 mm Hg of greater than 60 ml/minute. The coil wall thickness of about 0.002 inches adds 0.004 inches to the diameter of stent 18. The outer sheath 28, described infra, has a thickness of about 0.001 inches and produces an assembled stent 18 having an outside diameter of about 0.045 inches.

The design of the present invention provides a significant passageway 24 cross sectional area compared to the overall cross sectional area of stent 18. This parameter is important because only the stent 18 and balloon will typically traverse the stenotic site. The distal end of catheter body 12 (i.e., port 15) typically ends proximally of the stenosis in the preferred application.

This parameter is conveniently expressed in terms of the percentage of the outside diameter of stent 18 that the thickness of a single wall of stent 18 represents. In other words, in a preferred embodiment, a 0.003 inch wall thickness is about 6.7% of the 0.045 inch outside diameter.

Preferably, this percentage is less than about 14%, more preferably less than about 8%, and most preferably less than about 5% to optimized perfusion through the inflated balloon. Lower percentages may be achievable through the use of new materials or techniques not yet developed.

Lower percentages can be obtained by sacrificing pushability or by development or use of new high strength materials. For example, if sufficiently structurally sound for a given application, use of a 0.002 inch stent wall in a 0.045 inch diameter catheter will produce a 4.4% value. In addition, the percentage can be reduced by increasing the outside diameter of the stent to the maximum permitted for a given application.

Temporary stent 18 preferably comprises a support structure for resisting radial compression of passageway 24 by the inflated balloon 30. Suitable support structures include braided or woven polymeric or metal reinforcement filaments or a spring coil 26. Spring coil 26 preferably comprises a material having suitable biocompatibility and physical properties, such as a stainless steel or platinum wire. Alternatively, polymeric materials such as nylon or Kevlar (DuPont) may also be used. Preferably, rectangular ribbon is used, having cross-sectional dimensions on the order of about 0.001 inches by about 0.003 inches for small vessels, and on the order of about 0.005 inches by about 0.010 inches for use in larger vessels.

The wire or ribbon is preferably wound to produce a coil having an interior diameter within the range of from about 0.030 inches (coronary) to about 0.100 inches (periphery) and an exterior diameter within the range of from about 0.032 inches (coronary) to about 0.110 inches (periphery).

Spring coil 26 may be either "tightly wound" so that adjacent loops of coils are normally in contact with each other, or "loosely wound," as illustrated in FIG. 1, in which the adjacent loops of coil are normally separated from one another. The selection of a tightly wound or loosely wound coil for use in the present invention will be influenced by such factors as the desired weight of the finished catheter, the relative flexibility of the catheter in the region of temporary stent 18, and the amount of radially inwardly directed compressive force exerted by the inflation balloon 30, as will be apparent to one of skill in the art. Radiopacity may also be a factor.

Preferably, spring coil 26 is provided with an outer sheath or coating 28. Sheath 28 may be produced by dipping, spraying, heat shrinking or extrusion techniques which are understood in the art, and preferably comprises a relatively flexible material having sufficient biocompatibility to enable its use in contact with the vascular intima. Suitable materials for sheath 28 comprise linear low density polyethylene such as that produced by Dow, polyethylene terephthalate, nylons, polyester or other known or later developed medical grade polymers.

Figure 3:
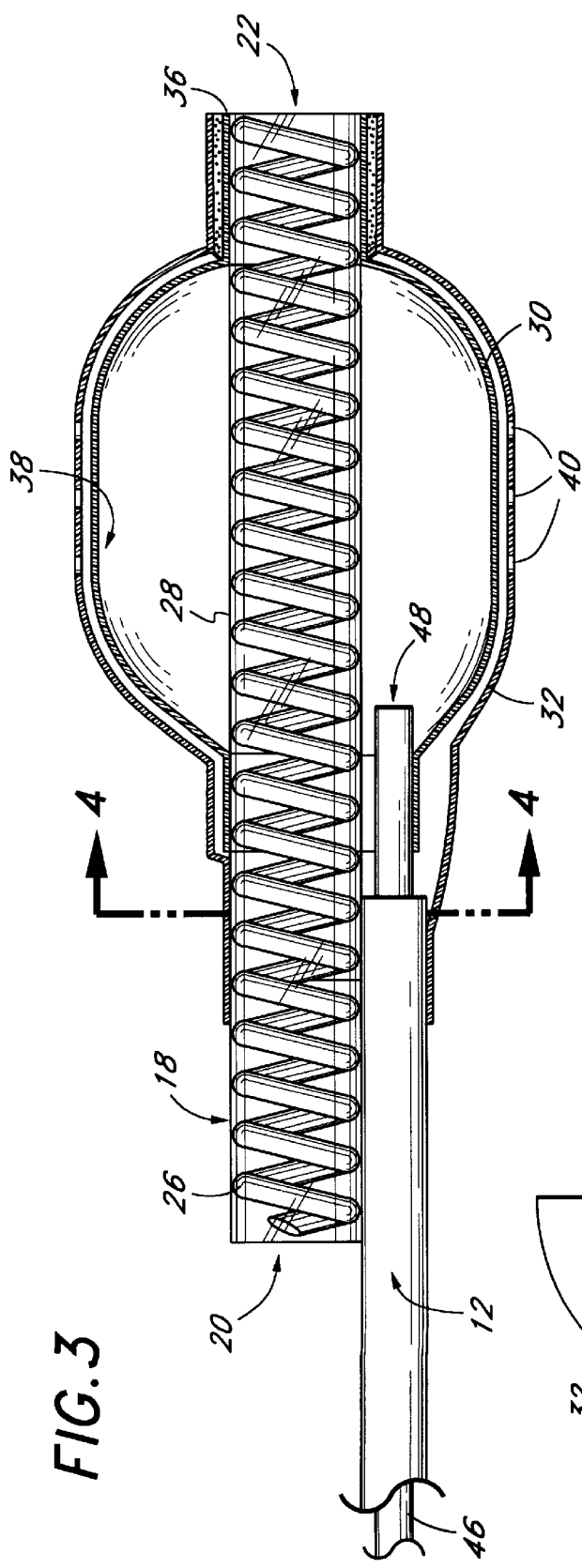
FIG. 3 is a partial sectional side elevational view of a second embodiment of the invention, having a coaxially configured catheter body.
Figure 4:
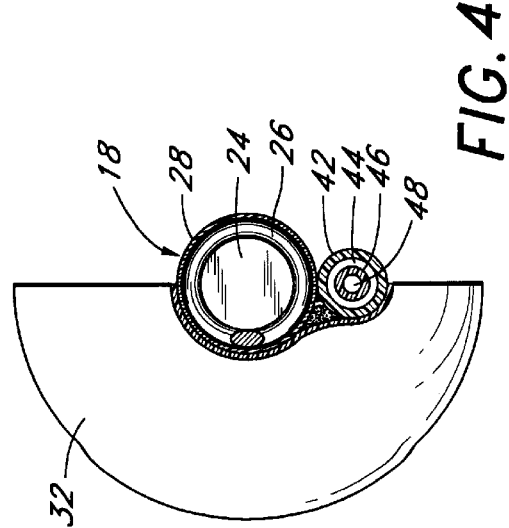
FIG. 4 is a cross-sectional view taken along the lines 4—4 in FIG. 3.

Inflation balloon 30 generally comprises a proximal neck portion 34, a distal neck portion 36 and an intermediate dilatation portion 38. Referring to FIGS. 1 and 3, it can be seen that the proximal neck of each balloon is larger in diameter than the distal neck to accommodate the catheter body 12.

Proximal neck portion 34 is tightly secured to the temporary stent 18 and distal portion of tubular body 12, such as by the use of conventional adhesives, thermal bonding or heat shrinking techniques. The interstitial space formed by the diverging walls of tubular body 12 and temporary stent 18 (in a circular cross section embodiment) may be provided with a fluid-tight seal such as by filling with adhesive. In this manner, a fluid-tight seal between the proximal neck portion 34 and the elongate tubular body 12 and temporary stent 18 is provided.

The distal neck 36 of inflation balloon 30 is provided with a fluid-tight seal with the distal portion of temporary stent 18. This seal may also be accomplished in any of a variety of manners known in the art, such as by the use of heat shrink materials, adhesives, or other thermal bonding or solvent bonding techniques. Preferably, distal neck 36 of inflation balloon 30 is heat shrunk onto stent 18.

As will be appreciated by one of skill in the art, the sheath 28 cooperates with the dilatation portion 38 of the inflation balloon 30 to provide a sealed compartment for retaining a dilatation fluid therein.

In a preferred embodiment of the illustrated design, the inflation balloon comprises a relatively non-elastic material such as linear low density polyethylene, polyethyleneterephthalate, nylon, polyester, or any of a variety of other medical grade polymers known for this use in the art. Preferably, the geometry, material and seals of balloon 30 will withstand an internal pressure of at least about 5 ATM and, preferably, about 10 ATM without any leakage or rupture.

Balloon 30 is preferably premolded to have an inflated diameter in a catheter intended for peripheral vascular applications within the range of from about 1.5 mm to about 8 mm. The balloon 30 in a catheter intended for coronary vascular applications preferably has an inflated diameter within the range of from about 1.5 mm to about 4 mm.

Although the present invention has been described in terms of an "inflation" balloon 30, it is to be understood that the balloon 30 can also function as a dilatation balloon, such as is well known in the art of percutaneous transluminal coronary angioplasty and other applications in which dilatation of a stenotic region in a body lumen is desired. In an embodiment of the present invention in which dilatation properties are desired, conventional dilatation balloon materials and design considerations can readily be incorporated, as will be understood by one of skill in the art. Alternatively, if the inflation balloon 30 is merely desired to provide sufficient radially expansive force to compress the delivery balloon 32 against the wall of the vessel, considerations appropriate for a lower pressure system may be utilized.

The delivery balloon 32 is most conveniently disposed radially outwardly from the inflation balloon 30. Delivery balloon 32 may comprise a generally non-elastic material such as is conventional for angioplasty dilatation balloons, or may alternatively comprise an elastic material such as latex or urethane, or any other suitably biocompatible elastomer. Use of an elastic material for delivery balloon 32 can assist in reducing the relatively rough edges of the collapsed inflation balloon 30, and thereby reduce trauma to the vascular intima during insertion and withdrawal of the catheter.

Delivery balloon 32 is provided with a plurality of delivery ports 40. Delivery ports 40 may be disposed radially symmetrically about the outer periphery of the delivery balloon 32, or may be limited to only portions of the exterior surface of the delivery balloon 32, depending upon the desired delivery pattern. For example, delivery ports 40 can be positioned only on one hemisphere of balloon 32. Alternatively, delivery ports 40 can extend for less than the entire length of the balloon, such as only in a central annular zone of the balloon, or only in one or both of the proximal and distal end zones of the balloon.

Delivery balloon 32 alternatively comprises a material which is inherently permeable, without the provision of discrete delivery ports 40. For example, woven or braided filaments or fabrics can be used. For relatively low delivery rate applications, fluid permeable membranes can also be used.

As can be seen with reference to FIG. 1 infusate introduced by way of lumen 16 is expressed by way of port 17 into the interior space of delivery balloon 32. The inflated volume of inflation balloon 30 causes the infusate to be expelled by way of ports 40 outside of the infusate delivery system.

Preferably, the relative inflated dimensions of the delivery balloon 32 and the inflation balloon 30 are such that a minimum amount of infusate is retained between the two balloons. Thus, preferably, the inflated inflation balloon 30 substantially completely fills the interior chamber of delivery balloon 32 to efficiently expel essentially all of the infusate fluid introduced into delivery balloon 32 by way of delivery lumen 16. Residual volume of infusate contained in lumen 16 can be expelled outside of the balloon such as by following the infusate with a small volume of normal saline or other 'rinse' solution, as will be understood by one of skill in the art.

In a further alternative, the inflation and infusate delivery are accomplished by the same balloon. In this embodiment, the permeability rate of the balloon material, or the diameter and number of delivery ports 40 are sufficiently small that the balloon is sufficiently firmly inflated without delivery at an excessive rate. Appropriate permeability rates for the balloon material can be determined through routine experimentation, in view of such factors as the viscosity of the infusate, desired delivery rate and the desired radially expansive force to be exerted by the balloon.

Figure 5:
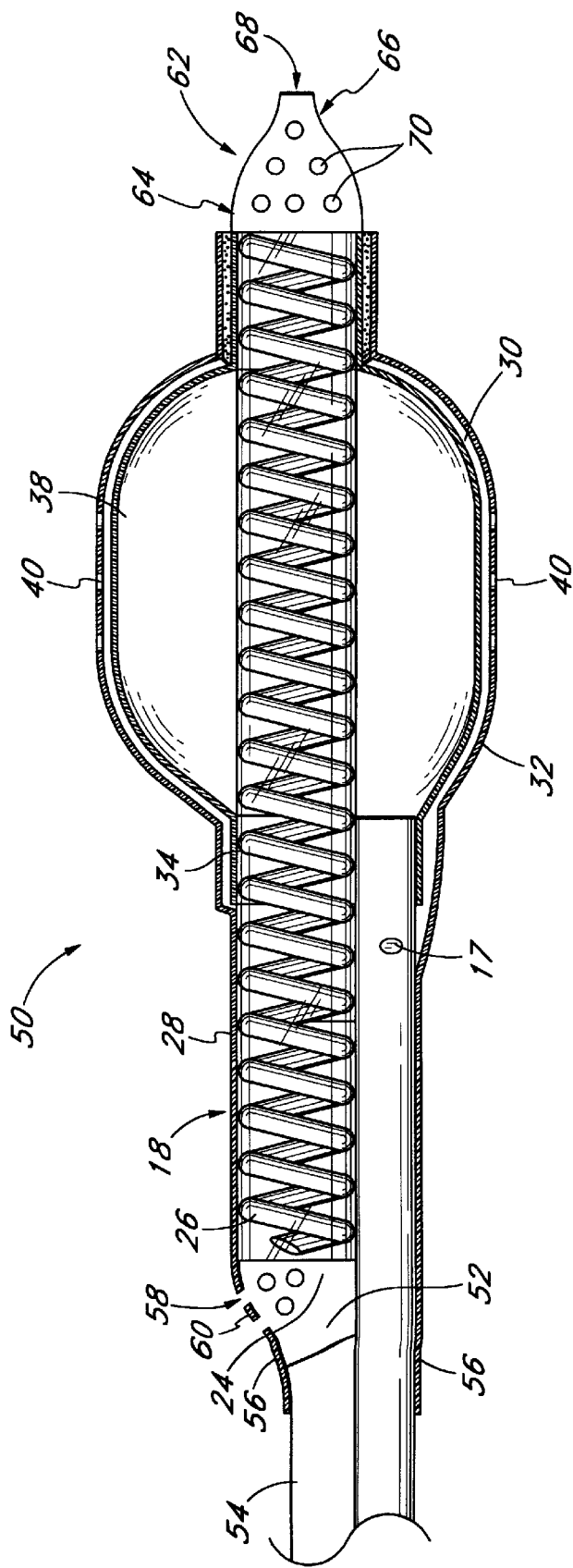
FIG. 5 is a partial sectional side elevational view of an over-the-wire embodiment of the present invention.

Referring to FIG. 5, there is disclosed an over-the-wire embodiment in accordance with the present invention. Over-the-wire catheter 50 is provided with a third lumen 52 extending through housing 54. In one embodiment, housing 54 comprises a separate tube which is secured along the outside of catheter body 12 such as by adhesives or other plastic bonding techniques known in the art. Preferably, however, housing 54 comprises an integrally formed three lumen catheter body as is well known in the art. Lumen 52 is provided with a sufficient interior cross-sectional area to axially slidably receive a conventional guidewire, such as a 0.014 inch guidewire.

In a preferred embodiment of the present invention, an extruded three lumen catheter body is prepared in accordance with techniques known in the art. One lumen, intended as guidewire lumen 52, has an internal diameter of at least about 0.016 inches. The wall surrounding lumen 52 is thereafter cut down using conventional cutting or grinding equipment. Alternatively, the catheter body is integrally molded with one lumen shorter that the other two, such as by injection molding about removable wire mandrels, and post molding cutting steps.

The distance between the distal end of lumen 52 and the proximal end of stent 18 can range from essentially zero up to an inch or more, particularly if a cover 60 is used as described infra. Preferably, however, the distance between the distal end of lumen 52 and the proximal end of stent 18 is no more than about 12 inches, and more preferably no more than about 0.2 inches.

In the embodiment illustrated in FIG. 5, the distal end of lumen 52 is about 0.08 inches from the proximal end of stent 18, and about 0.5 inches from port 15.

Preferably, a distal extension of the longitudinal axis of lumen 52 is aligned to extend through the lumen 24 in temporary stent 18. In this manner, a guidewire which is threaded distally through lumen 52 will thereafter be directed through lumen 24. This design facilitates removal and reinstallation of the guidewire while the catheter 50 is in place.

As an optional feature in accordance with the present invention, the proximal neck of one or both of the balloons 30, 32 extends in a proximal direction to form a seal 56 around housing 54. In this manner, a cover 60 is provided for the proximal end of lumen 24. Cover 60 can both assist in the withdrawal of the catheter from the vascular system, as well as assist in ensuring that a guidewire advanced distally through lumen 52 is guided into lumen 24. In an embodiment incorporating this feature, the cover 60 is provided with a plurality of perfusion ports 58 to permit continued perfusion through cover 60 and lumen 24. Preferably, the cover 60 comprises a proximal extension of delivery balloon 32.

As an additional optional feature in accordance with the present invention, there is provided a flexible, generally cone-shaped distal tip 62 for facilitating distal advancement of the catheter 50 along a previously positioned guidewire (not illustrated). Distal tip 62 comprises a relatively large diameter proximal portion 64 which is preferably an integral extension of either inflation balloon 30 or delivery balloon 32. Tip 62 tapers radially inwardly in a distal direction to a relatively narrow portion 66 having an axially-aligned guidewire and perfusion opening 68 therein.

The axial length of distal tip 62 may be varied depending upon a variety of factors such as the diameter and rigidly of the material used. In the preferred embodiment, distal tip 62 is made from the same material as delivery balloon 32, and may be formed by axially stretching the distal end of balloon 32 with the application of heat. The proximal port diameter is about 0.035 to 0.050 inches and the distal opening 68 in one embodiment has a diameter of about 0.016 inches. The axial length of tip 62 is about 0.4 inches.

To optimize perfusion through lumen 24, a plurality of ports 70 are distributed about the periphery of distal tip 62. Ports 70 in the preferred embodiment have a diameter of at least about 0.030 inches, and generally as many ports 70 (and ports 58) are provided as possible without unduly interfering with the structural integrity of the tip 62 (or cover 60). The precise configuration of distal tip 62 can be varied considerably, while still performing the function of providing a guide for the guidewire and permitting optimum perfusion through lumen 24.

Referring to FIGS. 6–10, there is disclosed a non-perfusion catheter embodiment 74 which also does not include a temporary stent. The non-perfusion embodiment 74 is preferably designed for use in percutaneous coronary transluminal angioplasty or other therapeutic or diagnostic procedures and adjunctive site specific intraluminal delivery of infusates.

The non-perfusion embodiment 74 preferably comprises a tubular body 12 which includes an inflation lumen 14, a delivery lumen 16, and a guidewire lumen 52. Two concentric balloons, an inner inflation balloon 30, and an outer delivery balloon 32 are connected to the tubular body 12. Alternatively, the inflation balloon and delivery balloon are disposed on opposing sides of the longitudinal axis of the body 12, such as for delivery of medication to an eccentric delivery site.

The inflation lumen 14 is in fluid communication with the inflation balloon 30 through port 15, the delivery lumen 16 is in fluid communication with the delivery balloon 32 through port 17, and the guidewire lumen 52 is in communication with a central lumen 75 which allows a guidewire to pass through the distal end of the catheter. A radiopaque marker 76 is preferably placed around the central lumen 75 in the center of the inflation balloon 32 to assist in positioning the catheter in the desired location. The tubular body 12 is preferably an integrally formed three lumen catheter body 78 as is well known in the art.

In one embodiment, the three lumen catheter body 78 has a triangular cross section for a majority of the length of the tubular body 12, as illustrated in FIG. 8. The triangular shape of the tubular body 12 provides a clearer fluoroscopy picture of the tubular body 12 within the patient, as the tubular shape reduces the cross sectional area of the tubular body 12 by up to 30%. The reduction in cross sectional area of the tubular body 12 thus allows for the injection of up to 30% more dye into the guiding tube (not shown) which provides a clearer fluoroscopy picture of the tubular body within the patient. Further, the reduction in cross sectional area of the tubular body 12 allows for more perfusion to occur around the catheter body 12. Alternatively, conventional circular or substantially circular cross section extruded catheter bodies can also be used.

Preferably, a distal extension of the longitudinal axis of the guide wire lumen 52 is aligned with a central lumen 75. In this manner, a guidewire which is threaded distally through lumen 52 will thereafter be directed through lumen 75. This design facilitates removal and reinstallation of the guidewire while the catheter 74 is in place.

As illustrated in FIG. 9, the central lumen 75 is typically concentric with both the inflation balloon 30 and delivery balloon 32 and extends through the center of the inflation balloon 30 and exits out the distal end of the catheter. The delivery lumen 16 extends into the catheter body and is in fluid communication with the delivery balloon 32. As described infra during infusion of a fluid into the delivery balloon a small luminal channel 79 is maintained between the inflation and delivery balloons 30, 32 to enable the flow of the infusate fluid to the delivery ports 40. The inflation lumen 14 terminates at the proximal end of the catheter body and is therefore not shown in FIG. 9.

The inflation and delivery balloons 30, 32 are preferably between about 2.0 cm and about 6 cm in length. However, balloon length can be varied depending upon the requirements of a particular desired application. The deflated profile of the inflation and delivery balloons 30, 32 is preferably between 0.025 inches and 0.070 inches in diameter. The inflation balloon 30 and delivery balloon 32 are sealed, using a process which will be described infra, such that a portion of the distal ends and a portion of the proximal ends of the balloons are sealed together.

The delivery balloon 32 preferably includes a series of discrete delivery ports 40 to enable the delivery of the infused liquid to the desired location. The delivery ports 40 are preferably between about 100 $\mu$m and 300 $\mu$m, and more preferably are about 250 $\mu$m in diameter. The discrete delivery ports 40 are preferably disposed radially symmetrically about the outer periphery of the delivery balloon 32 and cover the mid section of the balloon. Depending on the size of the delivery balloon 32 and the desired delivery profile there are preferably between about 3–50 delivery ports in the delivery balloon 32. Alternatively, fewer delivery ports 40 can be used and disposed only on one hemisphere of the balloon or only the center section, distal end or proximal end of the balloon or combinations thereof, depending on the desired delivery pattern.

The use of a relatively large total cross-sectional area of all of the delivery ports 40 and a relatively low pressure to infuse the infusate into the catheter results in a low outlet pressure at the ports 40 of the catheter tip and therefore causes the infusate to "weep" out of the ports 40 rather than exiting under a high pressure flow. The "weeping" action causes the infusate to exit the delivery balloon at a sufficiently low pressure that the infusate stream does not have enough force to penetrate the arterial wall beyond the elastic lamina layer. The delivery of the infusate while maintaining the structural integrity of the artery without the penetration of the infusate past the laminal wall of the artery will herein be referred to as intraluminal delivery, i.e., within the arterial lumen. Depending on the use of the catheter, i.e., for PTCA dilatation, for infusate delivery or for both operations, the inflation pressure of the inflation balloon 30 will influence the infusate delivery rate and penetration depth as described infra.

In another embodiment, the cross-sectional area of the individual delivery ports 40 and/or the total number of ports may be reduced to reduce the "weeping" effect and, combined with a higher pressure, enable a steady flow of the infusate to be delivered to the desired vascular site. In this manner, infusate can be forced into the vessel wall if that is desired. In a further embodiment, the size of the delivery ports 40 remains the same as described above and the infusate delivery pressure is simply increased to provide a steady penetrating flow of the infusate to the desired vascular location. Generally, for a low force delivery, the total cross sectional area of all ports is at least about 200% or 300% greater and typically no more than about 400% or 500% greater than the cross sectional area of the delivery lumen 16. The total area of the delivery ports 40 and the pressure of the media which is delivered to the vascular site can both be varied to achieve the desired delivery rate and force to the vascular site.

Infusate delivery using the non-perfusion embodiment 74 can be performed alone or in combination with a conventional PTCA procedure. When used in combination with a conventional PTCA dilatation operation, the infusate may be delivered before, during, or after the PTCA procedure.

When infusate delivery is performed before or after conventional PTCA, the inner inflation balloon 30 is inflated (before PTCA) or deflated (following PTCA) to a relatively low pressure, such as between about 0.4 ATM to about 1.5 ATM. preferable to about 0.5 ATM. A small luminal channel 79 (See FIG. 9) is maintained between the inner inflation balloon 30 and the outer delivery balloon 32. The luminal channel 79 is typically on the order of approximately 0.01 inches in diameter when the inflation balloon 30 is inflated to a constant 0.5 ATM. Channel 79 permits communication of the infusate from delivery lumen 16 to the outer ports 40 in the delivery balloon 32 at an even and continuous rate. As the pressure applied to the delivery media increases, the flow rate out of the ports 40 increases. The risk of a sufficiently high pressure to perforate the vascular wall can be minimized or maximized by appropriate sizing of the channel 79 with respect to the total cross sectional area of the ports 40 as will be readily understood by one skilled in the art.

When the inner inflation balloon 30 is inflated to between about 2 ATM and about 12 ATM or higher, the catheter can be used for dilatation of a stenosis using conventional PTCA techniques. During the PTCA procedure, an infusate can also be introduced into the delivery balloon 32 and delivered through the ports 40 to the specific location on the arterial wall. Even during the PTCA procedure, the resultant pressure within the delivery balloon 32 is not enough to deposit the infusate into the laminal layer of the arterial wall. Infusate delivery during a PTCA procedure may be advantageous to assist in treating the stenosis while the dilatation is occurring.

Once the infusate delivery and or PTCA procedure is complete and the catheter is prepared for extraction from the artery, the pressure is typically first reduced at the outer delivery balloon 32 to halt continual delivery of the infusate during extraction. However, the outer delivery balloon 32 may not immediately collapse. Next, the pressure in the inner inflation balloon 30 is reduced such as by aspiration with the inflation syringe, causing the inner balloon 30 to deflate. The inner and outer balloons 30, 32 are sealed together at both axial ends, as described below, thus the reduction in diameter of the inner balloon 30 reduces the profile of the outer balloon 32.

In the preferred embodiment, at least a portion of the inflation balloon 30 is connected to at least a portion of the delivery balloon 32. This structure permits the inflation balloon to "pull" the delivery balloon with it when the inflation balloon is being aspirated to minimize the external dimensions. The connection between the inflation balloon 30 and delivery balloon 32 can be accomplished in any of a variety of techniques as will be understood by one of ordinary skill in the art.

When only a relatively axially short delivery zone is required, the inflation balloon 30 and delivery 32 balloon can be heat sealed or otherwise bonded together along almost the entire axial length of the balloon, leaving only a relatively small unsealed area to allow the delivery of the infusate. To provide a relatively large (axially elongate) delivery zone, while maintaining the advantage of "pulling" the delivery balloon 32 in with the inner inflation balloon 30, only relatively small portions such as the very ends of the inflation balloon 30 and delivery balloon 32 can be sealed together.

In the present embodiment, preferably about 25% of the total axial length of the inflation balloon 30 is sealed to the delivery balloon 32 at the proximal end and about 25% of the total axial length of the inflation balloon 30 is sealed to the delivery balloon 32 at the distal end to aid in the deflation process as described above. Desirably, substantially the entire circumference of the distal ends of the inflation 30 and delivery balloons 32 are sealed together. Preferably, a relatively large percentage of the proximal ends of the inflation balloon 30 and delivery balloon 32 are circumferentially sealed together. The small portion of the two balloons 30, 32 on the proximal end that is not sealed together preferably forms the luminal channel 79 between the inflation balloon 30 and the delivery balloon 32.

FIG. 10 illustrates the non-perfusion embodiment 74 of the catheter in communication with a fluid delivery and guidewire entry apparatus 80. An inflation port 82 is provided for the delivery of the inflation fluid to the inflation lumen 14. A delivery port 84 is provided for delivery of the infusion fluid to the delivery lumen 16. Port 86 permits entry of a guidewire into the guidewire lumen 52. Preferably, the guidewire entry port 86 is positioned along the longitudinal axis of the catheter to easily align the guidewire with the guidewire lumen 52 to prevent any unnecessary bending of the guidewire during insertion into the lumen 52. Preferably, the fluid delivery and guide-wire entry apparatus 80 remains outside the patient so the doctor can control the delivery of the fluid and the guidewire from outside the patient's body. In an alternate embodiment, an indeflator (not shown), which is basically a syringe connected to a pressure reading device, is attached to the inflation and delivery ports 82, 84 to monitor the pressure of the fluid which is delivered to the inflation and delivery balloons 30, 32.

Catheters incorporating various features of the present invention can be manufactured in a variety of ways. Some of the preferred manufacturing techniques for catheters of the present invention are discussed below.

The perfusion conduit or temporary stent 18 assembly is manufactured by winding a coil of suitable spring wire, typically having a diameter or thickness dimension in the radial direction of the finished spring of about 0.002 inches. The wire is preferably wound about a mandrel sufficient to produce a spring having a lumen 24 with a diameter of about 0.039 inches.

The coil is preferably provided with an outer sheath or coating, as has previously been discussed. In one embodiment of the method of the present invention, the tightly coiled wire is held securely about the mandrel such as by clamping or soldering each end to the mandrel so that the coil is not permitted to unwind slightly and expand radially following release as will be understood by one of skill in the art. The tightly wound coil is thereafter inserted within a tubular sleeve, such as an extruded non-crosslinked polyethylene tubing of desired size. The spring coil is then released from the mandrel, so that the spring unwinds slightly within the polyethylene tube to produce a tight fit.

Typically, the minimum wall thickness of extruded polyethylene tubing as discussed above is no less than about 0.002 inches. This wall thickness can be reduced by heat stretching the polyethylene tubing either prior to insertion of the spring or directly onto the pre-wound spring coil to provide a tight seal. The heat stretching step of the present invention has been determined to produce a polyethylene coating on the spring coil having a wall thickness as low as about 0.001 inches. Thus, the overall diameter of the stent 18 assembly is reduced by about 0.002 inches.

The body of the catheter may be separately produced, typically by a combination of extrusion and post-extrusion processing steps. For example, an elongate triple lumen triangular cross section catheter body is produced by extrusion of high density polyethylene, to produce a body having a minimum wall thickness within the range of from about 0.003 to about 0.005 inches.

To minimize the overall cross sectional area of the assembled catheter, the distal portion of the tubular body 12 is reduced in diameter and wall thickness such as by axially stretching under the influence of heat. Stretching is accomplished by inserting, in a preferred embodiment, a 0.016 inch diameter pin in the guidewire lumen 52, and a 0.010 inch diameter pin in each of the inflation lumen 14 and delivery lumen 16. The distal end of the catheter body is thereafter heat stretched nearly to the limit before breaking. The result of the stretching reduces the cross-section of the triangular catheter body, from base to apex, from about 0.039 inches in the unstretched condition to about 0.025 inches following heat stretching.

The transition zone between the unstretched catheter body 12 and the distal axially stretched portion occurs within about 0.01 inches proximally of the proximal end of the temporary stent 18 in the assembled catheter. It has been determined by the present inventor that the decrease in structural strength of the heat stretched catheter body does not appear to adversely impact the integrity of the assembled catheter, in the designs disclosed herein.

The inflation balloon 30 and delivery balloon can be manufactured in any of a variety of manners which are now conventional in the art, such as free-blowing polyethylene, polyethylene terephthalate, nylon, polyester, or any of a variety of other medical grade polymers known for this use. Generally, the interior inflation balloon 30 is produced by blowing relatively long sections of cross-linked polyethylene within a mold to control the outside diameter. The use of cross-linked polyethylene facilitates heat sealing to the coil, which is preferably coated with non-crosslinked polyethylene.

The sections of inflation balloon material are thereafter heat stretched at the proximal and distal necks of a balloon down to a thickness of about 0.001 inches and a diameter which relatively closely fits the portion of the catheter body to which it is to be sealed. The appropriate length is cut, depending upon the desired length of the balloon and balloon necks in the finished catheter.

The proximal neck is heat sealed around the catheter body 12 and the temporary stent 18 as illustrated in FIGS. 1 and 5. In general, the length of the proximal and distal neck which is secured to the catheter body is within the range of from about 0.05 inches to about 0.1 inch, except in an embodiment such as illustrated in FIG. 5, in which the proximal and distal balloon necks are as long as necessary to accomplish their functions as a proximal cover or distal tip. The distal end of the inflation balloon 30 is thereafter heat sealed around the distal end of the temporary stent 18.

The outer balloon may thereafter be assembled in a similar manner, following "necking down" of the axial ends of the balloon by axial stretching under the application of heat. In an embodiment utilizing cross-linked polyethylene for the outer delivery balloon, the delivery balloon is typically secured to the axial ends of the inflation balloon through the use of a UV-curable adhesive, due to the difficulty in thermally bonding cross-linked polyethylene to cross-linked polyethylene.

However, it is to be understood that the material utilized for the outer delivery "balloon" may be varied considerably, and the term "balloon" as used in the context of the delivery balloon is intended to be only generally descriptive of this structure. For example, in addition to perforated balloons, a wide variety of materials not conventionally used for true balloons may also be used. Woven or braided fibers such as dacron, or fluid permeable membranes may desirably be used for the outer delivery balloon, as has been discussed.

In another alternate embodiment of the method and design of the present invention, the cross-sectional configuration of the temporary stent 18 changes from substantially circular at the distal end thereof to substantially rectangular or square at the proximal end thereof. This configuration is accomplished by winding the spring coil around a mandrel having a square cross-sectional portion, a transition portion, and a round cross-sectional portion. The transition portion on the resulting spring is located in the assembled catheter at about the line 4—4 on FIG. 3. This allows the temporary stent portion 18 to retain the same internal cross-sectional area, while reducing the maximum width of the assembled catheter.

Figure 11:
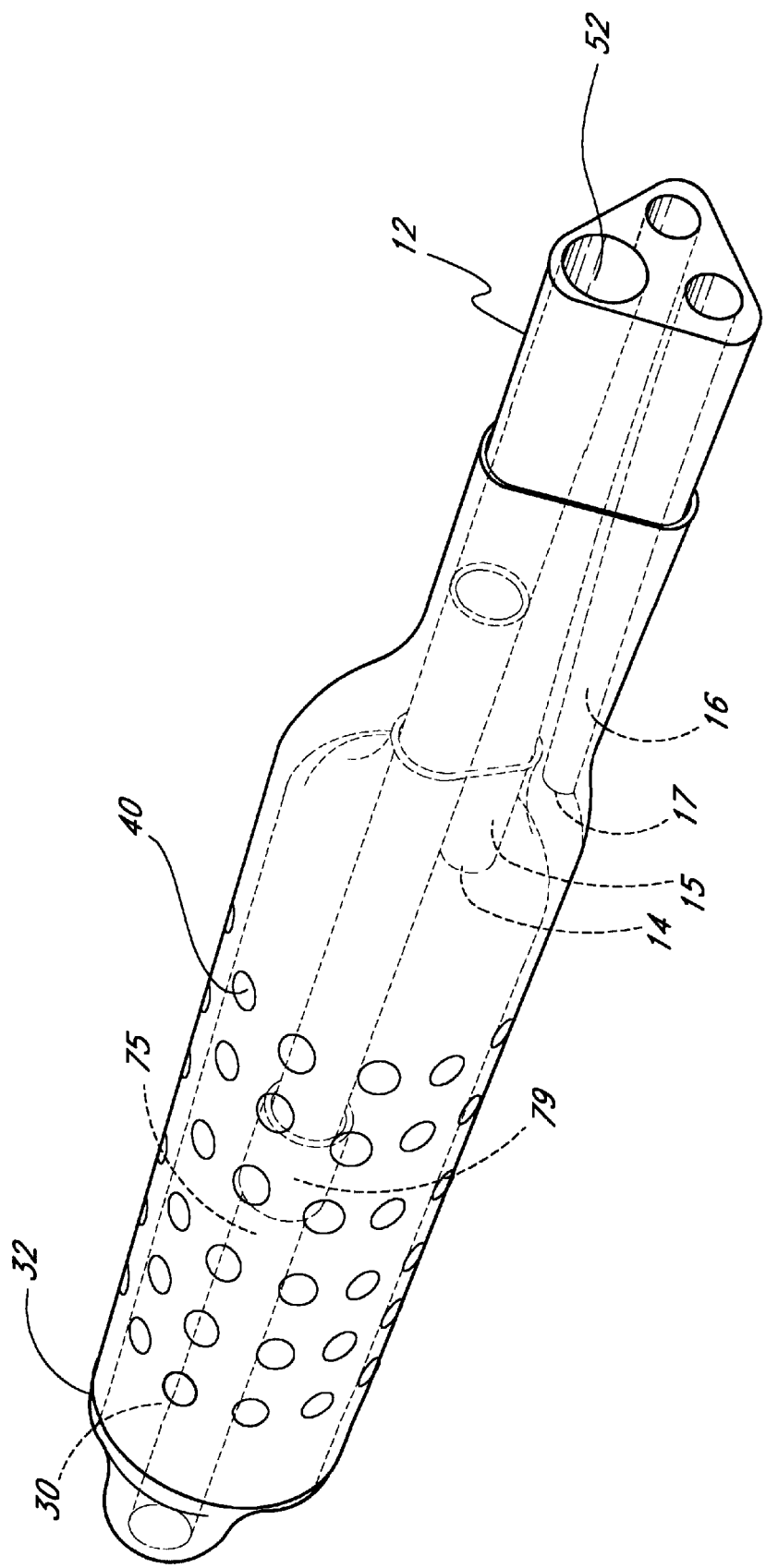
FIG. 11 is a perspective view of the non-stent embodiment of the present invention.

In the non-perfusion embodiment 74, the distal end of the catheter body 12 is cut away to separately expose each of the three lumen as illustrated in FIG. 11. First, a small portion of the catheter body is cut away to expose the delivery lumen 16. Next, a larger length is cut away to expose the inflation lumen 14. Finally, an additional portion is cut away to expose the guidewire lumen 52. The central lumen 75 abuts the guidewire lumen and the two lumen are joined together using an adhesive or any other suitable bonding process. A radio opaque marker 76 is preferably positioned in the center of the catheter 74 concentric to the central lumen 75.

A long steel mandrel is inserted into each of the inflation lumen 14, delivery lumen 16, and the guidewire lumen 52 which extends through the central lumen 75, the mandrels extending along the entire length of the catheter body 12. The steel mandrels are provided to keep the lumen from sealing closed during the balloon assembly procedure. The inflation balloon 30 is placed over the central lumen 75 and the inflation lumen 14. The inflation balloon 30 is then bonded to the central lumen 75 and the inflation lumen 14 at the proximal end and to the central lumen 75 at the distal end. The inflation balloon 30 is bonded to the inflation lumen 14 and the central lumen 75 using any of a variety of bonding techniques known to those skilled in the art, such as solvent bonding, thermal adhesive bonding, or by heat sealing. Preferably, in the present invention the inflation balloon 30 is heat sealed to the inflation lumen 14 and the central lumen 75.

Preferably the delivery balloon 32 is bonded to the catheter body 12 by any of a variety of bonding techniques such as solvent bonding, thermal adhesive bonding or by heat sealing depending on the type of balloon material used. In the present invention, crosslinked polyethylene balloons are used, therefore the inflation 30 and delivery balloons 32 are heat sealed together as follows. The wire mandrel is removed from the central lumen 75 and guidewire lumen 52 and a 0.01 inch diameter teflon rod is placed in the central lumen 75 to insure that the central lumen 75 is not sealed closed during the assembly process.

The delivery balloon 32 is positioned at the proximal end of the catheter 74 to cover the inflation balloon 30 and the delivery lumen 16. To create the luminal channel 79, a teflon rod of a diameter which is the same as the desired diameter of the luminal channel 79 is placed between the inflation balloon 30 and the deliver balloon 32 at the proximal end of the two balloons 30, 32. A teflon capture tube (not shown) is positioned over the delivery balloon 32 and covers the portion of the proximal end of the delivery balloon 32 which is to be sealed to the inflation balloon 30. The teflon capture tube is a generally tubular body which has approximately the same diameter as the inflated diameter of the inflation balloon 30 and is made of teflon. The inflation balloon 30 is inflated to a pressure which is sufficient to force the delivery balloon 32 against the wall of the teflon capture tube. Preferably, the inflation balloon 30 is inflated to about 30–50 psi. The capture tube is heated by any of a number of heating means such as electric coils or a furnace to a temperature which is sufficient to bond the two balloons 30, 32 together. In this case, the crosslinked polyethylene balloons are heated to a temperature of about 300° F. which causes both balloons to seal together. The teflon capture tube is then cooled to a temperature below the melting temperature of the two balloons 30, 32. The inflation balloon 30 is deflated and the catheter is removed from the capture tube. The teflon rod used to create the luminal channel 79 is removed.

To seal the distal end of the delivery balloon 32 to the inflation balloon 30, the delivery balloon is positioned at the distal end of the catheter 74 and completely covers the inflation balloon 30. The teflon capture tube (not shown) is positioned over the delivery balloon 32 and covers the portion of the distal end of the delivery balloon 32 which is to be sealed to the inflation balloon 30. The inflation balloon 30 is inflated to force the delivery balloon 32 against the wall of the teflon capture tube. Preferably, the inflation balloon 30 is inflated to about 30–50 psi. As above, the capture tube is heated by any of a number of heating means such as electric coils or a furnace to a temperature which is sufficient to bond the two balloons 30, 32 together. In this case, the crosslinked polyethylene balloons are heated to a temperature of about 300° F. which causes both balloons to seal together. The teflon capture tube is then cooled to a temperature below the melting temperature of the two balloons 30, 32. The inflation balloon 30 is deflated and the catheter is removed from the capture tube. The teflon rod is removed through the distal end of the central lumen 75. The steel mandrels are removed from the inflation lumen 14 and the delivery lumen 16 through the proximal end of the catheter body 12.

A conventional angioplasty guidewire is percutaneously transluminally inserted and advanced to the desired treatment site. Guidewires suitable for this purpose are commercially available, having a variety of diameters such as 0.014 inches.

The distal end 22 of temporary stent 18 is threaded over the proximal end of the guidewire once the guidewire has been positioned within the desired delivery site. The catheter 10 is thereafter advanced along the guidewire in the manner of conventional "over-the-wire" balloon angioplasty catheters. A conventional guidewire having an exterior diameter of about 0.014 inches has a cross-sectional area of about 0.000154 inches, and a temporary stent 18 having an interior diameter of about 0.039 inches has an interior cross-sectional area of about 0.001194 inches. The cross-sectional area of the interior lumen 24 of stent 18 which remains available for perfusion once a guidewire is in place is therefore about 0.00104 square inches.

The catheter 10 is advanced through the vascular system, along the guidewire, until the delivery balloon 40 is disposed adjacent the desired delivery site. Thereafter, a suitable inflation fluid such as a radiopaque solution is introduced by way of lumen 14 into the inflation balloon 30 to press the delivery balloon 32 against the vascular wall. Although described herein in its infusate delivery capacity, the catheter of the present invention may alternatively be used to perform dilatation, as has previously been described.

Once the delivery balloon 40 is positioned adjacent the vascular wall, medication is infused by way of lumen 16 in tubular body 12 and expelled through effluent ports 40 directly against the vascular wall. Medication or other media can be introduced under gravity feed alone, or by way of a positive pressure pump, as desired by the clinician in view of such factors as viscosity, adsorption rate, and desired delivery time.

In accordance with the foregoing structure and methods, infusion media such as that including microcapsules can be delivered directly to the affected site, with a minimal amount escaping into generalized circulation. The rate of delivery is somewhat limited by the rate of adsorption by the vascular wall, and delivery rates on the order of from about 1 ml per minute to about 20 ml per minute are presently contemplated for use in the method of the present invention. Certain infusates may be optimally delivered at much lower rates, such as 1 cc per day or lower. However, these rates may be modified significantly, depending upon the nature of the infusate, the nature of the type of site being treated, the extent to which "blowby" infusate fluid is permitted to escape into the circulatory system, or for any other factor relevant to the clinician.

In the delivery application, delivery of a sufficient amount of infusate may require an extended period of time. Perfusion past the delivery balloon by way of temporary stent 18 minimizes the adverse impact on circulation due to the indwelling delivery catheter. Alternatively, any of a variety of alternative perfusion structures can be provided on the delivery catheter. One suitable perfusion design is shown in U.S. Pat. No. 5,571,089 issued Nov. 5, 1996 to Crocker, the disclosure of which is incorporated in its entirety by reference. Following infusion of the predetermined volume of the agent, over the predetermined infusion time, the inflation balloon 30 is deflated and the catheter may be withdrawn.

During the foregoing procedures, the guidewire (not illustrated) may either be removed or may be left in place, as will be understood by one of skill in the art. In general, cardiologists prefer to leave the guidewire in place so that the catheter may be withdrawn and repositioned, or replaced by other catheters.

In accordance with a further aspect of the method of the present invention, the catheter 10 is utilized as a temporary stent for an observation period following percutaneous transluminal coronary angioplasty, atherectomy, laser ablation or any of a variety of other interventional catheter techniques and procedures. In an embodiment of the apparatus for use with this aspect of the method of the present invention, the delivery balloon 32 may be deleted entirely, and the tubular body 12 may optionally be provided with only a single fluid lumen extending therethrough to provide communication with the interior of inflation balloon 30.

Following removal of an interventional therapeutic catheter, such as an angioplasty, atherectomy or laser ablation catheter, the temporary stent catheter 10 is inserted along the guidewire or through an introduction sheath and disposed with the inflation balloon 30 at the previously treated site. Inflation balloon 30 is inflated to the desired diameter to resist reocclusion during a post-procedure period. Such observation periods may vary depending upon the circumstances of the patient and the cardiologist, but generally range from about 30 minutes to about 24 hours. During this time, perfusion across the inflation balloon 30 is permitted by way of temporary stent 18.

As has been previously described, the relative cross-sectional area of the lumen 24, even with an indwelling guidewire, permits a significant degree of perfusion to occur. In addition, the longitudinal axis of lumen 24 is generally concentric with or parallel to the longitudinal axis of the artery or vein in which the indwelling temporary stent is disposed. In this manner, the interruption of direction of blood flow is minimized, thereby reducing the likelihood of damaging blood cells and introducing undesired turbulence.

One preferred infusate is in the form of microcapsules. The microcapsules are preferably sized and configured for delivery to a treatment site, and retention at that site for a predetermined therapeutic or diagnostic time period. Following the predetermined time period, the microcapsules are preferably dissolved or dissipated so that no residual remains.

The microcapsules are preferably large enough to lodge among smooth muscle or other cells, at the target site, and not be disrupted by microcirculation in the tissue. The microcapsules are also preferably sufficiently small that they can migrate into fissures or other injury sites in the vascular lamina, such as the type the inventors believe are typically incurred during a mechanical dilatation of the vessel. Preferably, the microcapsules have an average width within the range of from about 5 microns to about 50 microns, and, more preferably, within the range of from about 10 microns to about 30 microns. In one embodiment, the microcapsules have an average diameter of about 20 microns with an outer shell having a wall thickness of from about 3–5 microns. Other sizes or blends of different sizes may alternatively be used, depending upon the intended use and the nature of the active core or outer shell as will be apparent to those of skill in the art in view of the disclosure herein.

The composition of the microcapsule core and outer shell can be varied widely, depending upon the desired active agent to be delivered, and the length and profile of the desired delivery period. For example, the core or shell can consist of or include any of a wide variety of active agents such as pharmaceutical agents, imaging agents, or other therapeutic or diagnostic materials. In one preferred embodiment, the therapeutic agent comprises a source of radiation, such as for use in minimizing or delaying the onset of restenosis following a vascular dilatation. Radiation sources which emit alpha or beta radiation are preferred, although alpha radiation may be too short ranged for some applications. In addition, sources which produce radiation for a relatively short time period, such as less than about four weeks, and preferably less than about 15 days, will be preferred for many clinical applications.

In one embodiment, the radiation source comprises Phosphorous-32, ($^{32}$P) which is a beta emitter having a half life of 14 days. Phosphorous-32 is additionally advantageous because many of its phosphate forms are completely water soluble, and will leave no incompatible residual in the body. Other radioactive sources may also be used, such as Molybdenum-98, which can be encapsulated in a stable form and converted to Technetium-99 for imaging with a gamma camera. More potential sources of alpha or beta radiation include $^{67}$Cu, $^{90}$Y, $^{131}$I, $^{45}$Ca, and $^{211}$At.

The $^{32}$P in the form of polyphosphate, orthophosphate, phosphate, a salt, etc. may be dissolved in a water/saline solution and then suspended in a PGLA solution prepared in methylene chloride.

The $^{32}$P or other radiation source is typically contained in the inner core and preferably completely encased in an outer shell made of a transient material, such as water soluble or biodegradable materials. The purpose of the outer shell in the case of a $^{32}$P core is to delay dissolution of the core until a sufficient predetermined period of time has passed. The outer shell preferably has a wall thickness, density or other parameters which are sufficient, in view of the solubility characteristics of the shell material, to prevent contact between the phosphorous core and body fluids for a predetermined period of time.

Any of a variety of transient materials can be utilized to form the outer shell of the microcapsule of the present invention, depending upon the composition of the inner microcapsule core and the desired degradation time. Suitable shell materials can be determined through routine experimentation by those of skill in the art, in view of the disclosure herein.

In general, useful polymeric shell materials include a variety of polymers. copolymers, block copolymers and mixtures thereof which are soluble or biodegradable with little or no residual. Polymers or polymer classes which may be useful include poly(glycolic acid) (PGA), poly(lactic acid) (PLA), poly(glycolic lactic acid (PGLA), polydioxanes, polyoxalates, poly(alpha-esters), polyanhydrides, polyacetates, polycaprolactones, poly (orthoesters), polyamino acids, polyurethanes, polycarbonates, polyiminocarbonates, polyamides, poly (alkyl cyanoacrylates), and mixtures and copolymers thereof. Additional useful polymers may include stereopolymers of L- and D-lactic acid, copolymers of bis(p-carboxyphenoxy) propionic acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxyalkanoates, polysaccharides and mixtures thereof. Additional useful materials include gelatin, modified starch, gum arabic, and lipids and mixtures thereof. Binary and ternary systems are contemplated. The outer shell may also contain active agents.

In one embodiment, the outer shell comprises polyglycolic lactic acid (PGLA). PGLA is a biocompatible compound that retains a stable protective shell during delivery until biodegradation. PLA and PGA are conventionally prepared by either condensation polymerization of the free acids or by catalytic, ring-opening polymerization of the dilactones. Both PLA and PGA are environmentally compatible because they degrade respectively to lactic acid and glycolic acid, both natural and normally harmless products.

Biodegradation of poly(glycolic acid) and poly (DL-lactic acid), for example, has been well documented in the literature. The degradation mainly takes place through the hydrolysis of the ester bond; the reaction is second order and highly pH dependent. The rate constant at pH 10 is 7 times faster than that at pH 7.2. The ability to create microcapsules with different degradation times by varying the ratio of glycolic acid and lactic acid monomers, adding one or more other monomers to the blend, substituting one or more monomers for glycolic acid and/or lactic acid, using different polymerization methods to obtain various types of copolymers such as block or random copolymers, and utilizing polymer chains of varying lengths, will be appreciated by one of skill in the art.

Figure 12:
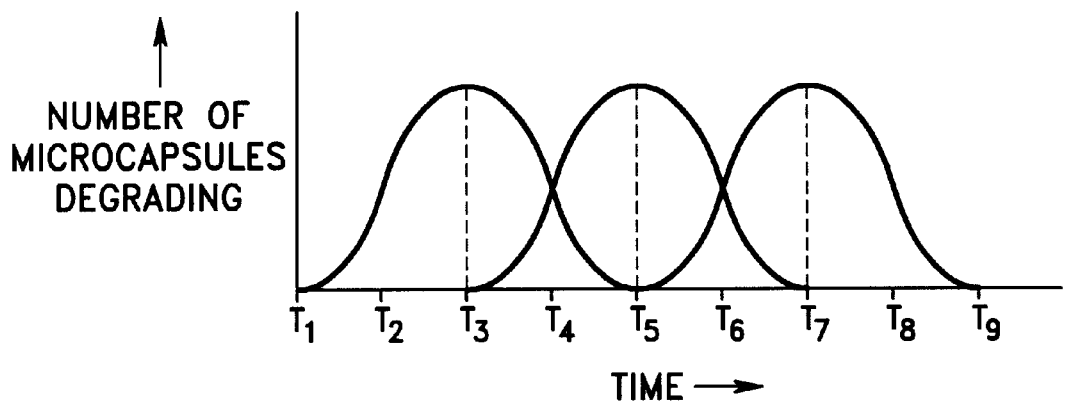
FIG. 12 is a depiction of the degradation over time of a preferred combination of three species of microcapsules with different dissolution or degradation times.
Figure 13:
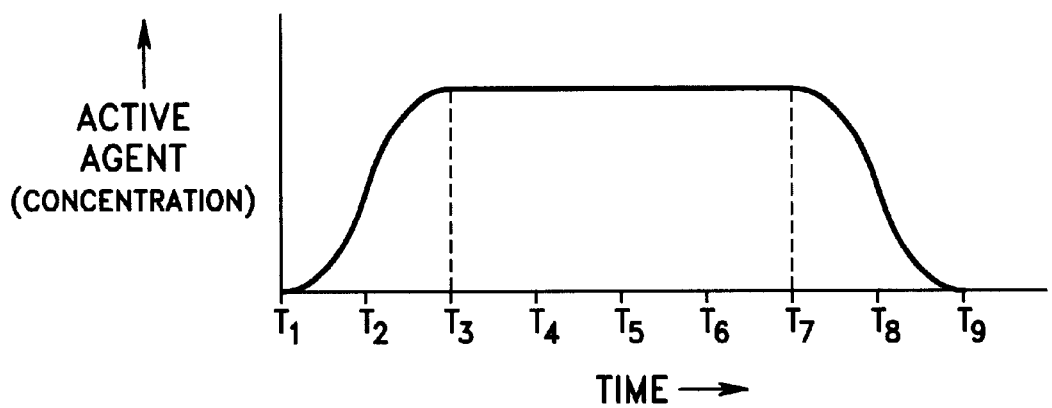
FIG. 13 is a depiction of how the concentration of active agent varies over time when a preferred combination of three species of microcapsules is administered.

By mixing microcapsules with different degradation times, infusable formulations can be created which achieve unique release profiles of an active agent from the inner cores of the microcapsules as they degrade or dissolve. For example, a formulation can be prepared containing three different microcapsule populations with the same inner core active agent, but each with different outer shell degradation times. The cores of each microcapsule population would become exposed to the surrounding blood or other environment according to a profile similar to that in FIG. 12, creating a total concentration of active agent at the treatment site as a function of time like that shown in FIG. 13. Thus, a sustained, relatively constant release of the active agent is achieved at the target site for a period of time, as illustrated in FIG. 13.

In one preferred embodiment, a formulation containing three different populations of microcapsules, A, B, and C, are made in which all the microcapsules have the same quantity of a given active agent in their inner cores and where the degradation time of A is the shortest and C is the longest. Upon administration at time $T_1$, microcapsules in groups A, B, and C all begin to degrade. None of the microcapsules have broken to release any active agent at this time, so the concentration of active agent for types of active agent which do not penetrate the shell is zero. The Group A microcapsules have the shortest degradation time, and they begin to break and release their dose of active agent at time $T_2$. At time $T_3$, the Group A microcapsules have reached their average degradation time, and the maximum number of them are degrading and releasing their dose of active agent as depicted in FIG. 12. This also results in a maximum concentration of active agent at this point on FIG. 13. As time $T_4$ is reached, the last of the Group A microcapsules are releasing their contents while the Group B microcapsules are beginning to release active agent. When the dosages released by Groups A and B are combined at $T_4$, the total concentration of active agent at the treatment site is approximately the same as at $T_3$, as seen in FIG. 13. Moving toward time $T_5$, as the Group A microcapsules decline in number, more Group B microcapsule shells degrade, keeping the concentration of active agent at a fairly constant level. At time $T_6$, the degradation of the Group B microcapsules reaches its maximum, and the Group A particles have been consumed. This same basic pattern seen for Groups A and B is repeated for Groups B and C, and once $T_7$ is reached, the concentration of active agent begins to decline as the Group C microcapsules finish degrading. This same pattern may be used for a smaller or larger number of groups of microcapsules, depending upon the composition of the microcapsules, the active agent and the clinical application, among other factors.

Different delivery profiles for the active agent may be created by incorporating the active agent into the outer shell of the microcapsules so that it is slowly released as the microcapsules dissolve or degrade, or by coating the active agent onto the outer shell of the microcapsules for immediate release upon administration. One of skill in the art will appreciate that any or all of the aforementioned techniques may be combined to create a delivery profile for the active agent that is most suited to a particular clinical application.

The microcapsule can be manufactured in accordance with any of a variety of techniques which are understood in the microencapsulation field. Choice of technique may depend upon the materials chosen for the core and shell, the desired thickness of the shell, and the desired size of the resulting microcapsules, among other factors. Three such manufacturing techniques are solvent evaporation/extraction, centrifugal extrusion, and the rotating disk method.

Figure 14:
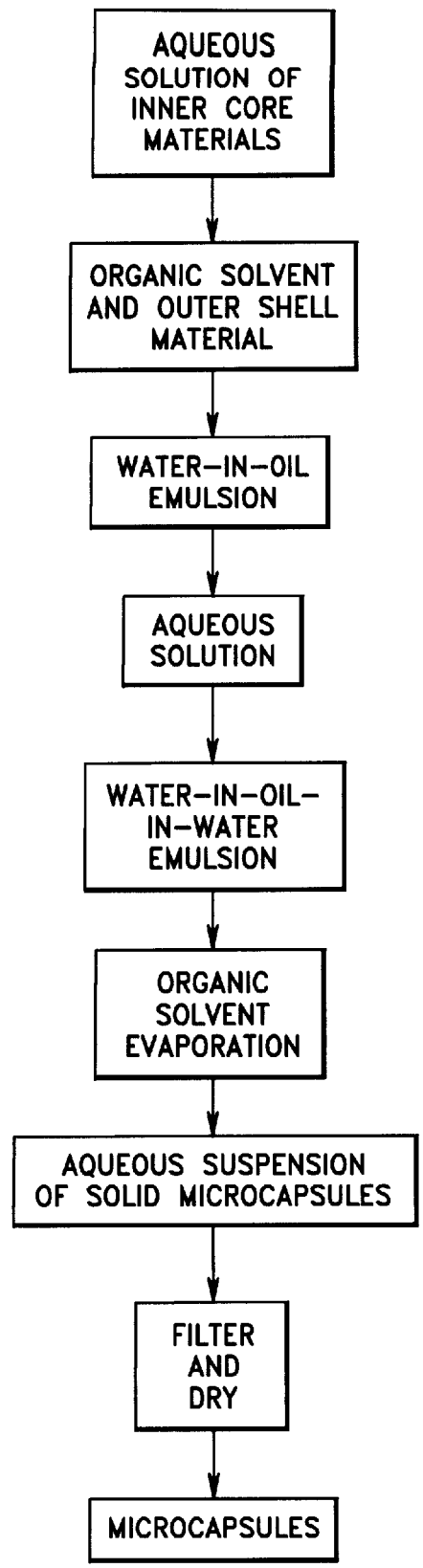
FIG. 14 is a pictorial representation of how microcapsules are created using the solvent evaporation technique.

The solvent evaporation technique works by exploiting differences in solubility and miscibility of solvents and the materials that form the outer shell and inner core of the microcapsule. A pictorial representation of the solvent evaporation technique is presented in FIG. 14. The materials that are to form the inner core are placed into aqueous solution. This aqueous solution is then poured into a solution of polymer in an organic solvent, such as methylene chloride, to form a water-in-oil emulsion. The polymer in solution will form the outer shell of the microcapsule and the organic solvent is preferably immiscible with water with a high vapor pressure and a boiling point of less than 100° C. The water-in-oil emulsion is then itself emulsified in an aqueous solution containing a surfactant, such as TWEEN 20, to form a water-in-oil-in-water emulsion. Heat and/or reduced pressure is applied to the emulsion while it is stirred to facilitate evaporation of the organic solvent. This procedure results in the formation of solid microcapsules, which may be recovered by drying, freeze drying, centrifugation or filtration. Capsules will then preferably be washed and dried for storage. More layers may be added to the microcapsule by continuing to alternate aqueous and organic emulsification solutions.

The solvent extraction technique differs from the solvent evaporation method only in that the organic solvent is removed by extraction rather than by evaporation before the microcapsules are recovered. The extraction is done by several methods including: using a large quantity of final aqueous solution as compared to the volume of the water-in-oil emulsion; choosing an organic solvent system where one of the solvents in the system has a greater affinity for the final aqueous solution; or choosing a final aqueous solution that includes a component which acts as an extractor of the organic solvent but is immiscible with the outer shell material.

The proper solvent systems and additives to use for any given combination of inner core and outer shell materials and can be readily determined through experimentation. One of skill in the art will also appreciate that the size of the inner core and the thickness of the outer shell may be varied by alterations in technique, conditions, and materials. One potential modification is the addition of one or more agents such as gelatin to increase the viscosity of the aqueous solution which forms the inner core, thus reducing any potential diffusion of active agents from the inner core through the outer shell material into the final aqueous solution during the final emulsification step.

The centrifugal extrusion technique involves coextrusion of two immiscible liquids from concentric openings on a rotating nozzle. The material which forms the inner core is pumped through the inner opening on the nozzle and the material which forms the outer shell is pumped through the outer opening. As the nozzle spins, the column of coextruded liquids breaks up into a stream of spherical droplets, each one having the inner core materials encased by a layer of outer shell material. The correct frequency for the spinning of the nozzle is readily determined by experimentation, and varies according to materials used, size of the openings, viscosity, temperature and other factors. The liquid which forms the outer shell should be capable of hardening rapidly in order to facilitate the formation of the microcapsules. Some examples of hardening techniques are: collecting the particles in a bath of liquid in which they are insoluble; allowing sufficient flight time or projecting the microcapsules into a mist of chilled fluid to allow them to cool; or exposing the droplets to heat to facilitate solvent evaporation. Both inner core and outer shell materials should have a relatively low viscosity and be made of materials that minimize tailing or stringing between droplets as they are formed.

In the rotating disk method, the inner core materials are dispersed in a liquid composed of the outer shell materials, and this suspension is slowly poured onto a rotating disk. The inner core particles, thus coated with a film of the outer shell material, fly off the edge of the disk upon contact. The outer shell may be solidified by a number of methods, including those discussed above for hardening of outer shells of microcapsules formed by centrifugal extrusion. The rotating disk is an effective method of encapsulating inner core materials that are solid-like under the conditions of the formation process. Best results are achieved when using inner core materials that are at least roughly spherically shaped.

If desired, the outer shell of the microcapsules may be coated with an additional material. Such materials may include an active agent, or a passive agent such as to improve product stability or increase in vivo resistance to degradation. In one embodiment, the outer shell of the microcapsules is coated with an anticoagulant such as heparin to inhibit clotting of blood, and/or smooth muscle cell growth, at a treatment site. In another embodiment, the microcapsule is coated with a substance, such as an amine, to enable the microcapsules to have improved tissue adhesion at the delivery site. Other such materials may include adding a charge to the surface for the purpose of having the microspheres repel each other or the constitutents of blood. An outer coating may be applied by immersion, spraying or other coating techniques which will be apparent to those of skill in the art.

Microcapsules thus formed may be stored for future use. Preparation for storage of microcapsules includes drying in small dose-sized quantities, which may be by freeze drying or any conventional drying process based on sublimation of water.

In one embodiment, microcapsules are configured to deliver a predetermined dose of radiation to an intraluminal treatment site. The microcapsule is provided with an inner core that contains an active agent which emits therapeutic radiation, and an outer protective shell. One convenient and practical method of accomplishing this is by neutron activation of microcapsules containing $^{31}$P.

An inner core formulation containing $^{31}$P is encapsulated in accordance with any of the known techniques, such as those disclosed above. Following the microencapsulation of the $^{31}$P, the $^{31}$P core can be converted to therapeutic $^{32}$P, for example, by exposing the microcapsules to a neutron flux of about $10^{10-13}$ neutron/cm$^2$s for about half an hour or longer from a neutron beam source such as a reactor.

This technique enables the production of stable microcapsules for activation at a later date to a selected dose level, thus avoiding handling and storing radioactive materials during production. The microcapsules are preferably shipped in a neutral, dry form, and activated at the clinical site just prior to use. Additionally, TWEEN 20 can be used as a stabilized surfactant so as to prevent particule agglomeration. A useful concentration of TWEEN 20 would be about 0.25% V/W in saline or deionized water. One additional benefit of neutron activation at the clinical site is the sterilization of the microcapsules. Neutron beam sterilization is a well known and effective means of sterilizing solids utilized by manufacturers of medical devices and implants.

Microcapsules according to the disclosure herein may be used for a variety of therapeutic and/or diagnostic purposes other than vascular proliferative disorders, such as for treatment of tumors. Moreover, the use of microcapsules permits delivery of several drugs at varied time intervals, allowing for localized, multi-drug clinical treatments. A wide variety of application modes may be used, as will be apparent to those of skill in the art, such as injection of the microcapsules into the treatment site, and spraying or brushing the microcapsules onto the skin or inside the body during an open surgical procedure.

The infusate will preferably consist of microcapsules suspended in a physiologically acceptable liquid to facilitate movement through a catheter or syringe. The concentration of such suspensions may vary within wide limits depending on the intended use, preferably between about 1% and about 50%. Such physiologically acceptable liquids may include the usual fluids for intravascular injection, for example a saline solution (0.9% aqueous NaCl), water solutions of glucose, sorbitol, dextrose, or other sugars or sugar derivatives, solutions of salts naturally present in blood plasma, or so-called plasma expanders. Other physiologically acceptable substances include PVP (polyvinylpyrrolidone) sold under the trade designation Plasdone K-30 and Povidone by GAF Corp., and drugs or medications. Small quantities of other substances, such as surfactants or emulsifiers that are not harmful to humans when present in a small quantity, may also be added. In approximate terms, 5 ml of 20 micron spheres would include about two billion microcapsules.

What is claimed is:

1. A two-component microcapsule for therapeutic or diagnostic use comprising:

a first part comprising a transient radioactive central core; and a second part comprising a transient single-piece outer shell surrounding the central core; wherein the microcapsule has a diameter within the range of from about 5 microns to about 50 microns, and the central core and the outer shell break down in an aqueous environment into biologically compatible break down products.

2. A microcapsule according to claim 1, wherein the thickness of the outer shell is within the range of from about 1 micron to about 15 microns.

3. A microcapsule as in claim 1, wherein the core comprises an isotope of phosphorous.

4. A microcapsule as in claim 3, wherein the isotope of phosphorous is selected from the group consisting of phosphorous-31, phosphorous-32, and phosphorous-33.

5. A microcapsule as in claim 1, wherein the shell comprises a transient barrier for preventing contact between the core and a surrounding aqueous environment for a predetermined period of time.

6. A microcapsule as in claim 1, wherein the core comprises a beta-emitting or gamma-emitting species.

7. A microcapsule as in claim 1, wherein the microcapsule is made by a process comprising the steps of:

(a) making an aqueous solution comprising materials to form the central core of said microcapsule;

(b) placing the aqueous solution into a non-aqueous solution comprising organic solvent and materials to form the outer shell of said microcapsule to form an emulsion wherein droplets of aqueous solution are surrounded by the non-aqueous solution;

(c) placing the emulsion formed in step (b) into a second aqueous solution comprising a surfactant;

(d) removing the organic solvent to form microcapsules, wherein the materials to form the outer shell are deposited on the central cores formed from the droplets of aqueous solution, and (e) recovering the microcapsules.

8. A microcapsule as in claim 7, wherein the organic solvent is removed by a method selected from the group consisting of evaporation and extraction.

9. A microcapsule as in claim 1, wherein the microcapsule is made by a process comprising the steps of:

preparing a first solution and a second solution, the first solution comprising materials to form the central core and the second solution comprising materials to form the outer shell, wherein the first solution and second solution are generally immiscible; and expressing a stream comprised of the first and second solutions from concentric openings on a rotating nozzle, wherein the second solution is expressed about the first solution and the nozzle is rotated at a speed sufficient to cause the stream to break into droplets which form microcapsules, wherein the first solution is encased by a layer of the second solution.

10. A two-component microcapsule for therapeutic or diagnostic use comprising:

a first part comprising a transient radioactive central core; and a second part comprising a transient single-piece outer shell surrounding the central core; wherein the central core and the outer shell break down in an aqueous environment into biologically compatible break down products;

wherein the thickness of the outer shell is within the range of from about 1 micron to about 15 microns.

11. A microcapsule according to claim 10, wherein said microcapsule is within the range of from about 5 microns to about 50 microns in diameter.

12. A microcapsule as in claim 10, wherein the core comprises an isotope of phosphorous.

13. A microcapsule as in claim 12, wherein the isotope of phosphorous is selected from the group consisting of phosphorous-31, phosphorous-32, and phosphorous-33.

14. A microcapsule as in claim 10, wherein the shell comprises a transient barrier for preventing contact between the core and a surrounding aqueous environment for a predetermined period of time.

15. A microcapsule as in claim 10, wherein the core comprises a beta-emitting isotope.

16. A microcapsule as in claim 10, wherein the microcapsule is made by a process comprising the steps of:

(a) making an aqueous solution comprising materials to form the central core of said microcapsule;

(b) placing the aqueous solution into a non-aqueous solution comprising organic solvent and materials to form the outer shell of said microcapsule to form an emulsion wherein droplets of aqueous solution are surrounded by the non-aqueous solution;

(c) placing the emulsion formed in step (b) into a second aqueous solution comprising a surfactant;

(d) removing the organic solvent to form microcapsules, wherein the materials to form the outer shell are deposited on the central cores formed from the droplets of aqueous solution; and (e) recovering the microcapsules.

17. A microcapsule as in claim 16, wherein the organic solvent is removed by a method selected from the group consisting of evaporation and extraction.

18. A microcapsule as in claim 10, wherein the microcapsule is made by a process comprising the steps of:

preparing a first solution and a second solution, the first solution comprising materials to form the central core and the second solution comprising materials to form the outer shell, wherein the first solution and second solution are generally immiscible; and expressing a stream comprised of the first and second solutions from concentric openings on a rotating nozzle, wherein the second solution is expressed about the first solution and the nozzle is rotated at a speed sufficient to cause the stream to break into droplets which form microcapsules, wherein the first solution is encased by a layer of the second solution.

* * * * *